United States Patent
Matsushita et al.

(10) Patent No.: US 6,452,046 B2
(45) Date of Patent: Sep. 17, 2002

(54) PROCESS FOR PRODUCING 2,3,5,6-TETRACHLORO-1,4-BENZENEDICARBOXYLIC ACID

(75) Inventors: Utaro Matsushita; Kimitoshi Sano, both of Yokohama; Kenichi Komatsubara; Teruhiko Ishii, both of Tsukuba, all of (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 09/791,323

(22) Filed: Feb. 22, 2001

(30) Foreign Application Priority Data

Mar. 3, 2000 (JP) ......................... 2000-059196

(51) Int. Cl.$^7$ ................. A01N 37/10; C07C 51/09; C07C 51/08
(52) U.S. Cl. ................. 562/483; 562/484; 504/144
(58) Field of Search ................. 562/483, 484; 504/144

(56) References Cited

U.S. PATENT DOCUMENTS 2,923,634 A * 2/1960 Lindemann .................. 71/2.6

FOREIGN PATENT DOCUMENTS

GB 1317064 * 5/1973

OTHER PUBLICATIONS

"The Chlorination of Isophthaloyl and Terephthaloyl Chloride" Rabjohn, N., J. Am. Chem. Soc. 70, p. 3518(1948).*
Organic Chemistry, 2d Ed., Morrison and Boyd, pp. 585–587 and pp. 670–671. (1971).*
The Pesticide Manual, 9$^{th}$ ed., Charles R. Worthington, editor. p. 171. (1991).*
"o–Toluic Acid", Organic Synthesis Col. vol. 2, pp. 588–589 (1943).
"Mesitylacetic Acid", Organic Synthesis col. vol. 3, pp. 557–559 (1955).

* cited by examiner

Primary Examiner—Mukund J. Shah
Assistant Examiner—Zachary C. Tucker
(74) Attorney, Agent, or Firm—Webb Ziesenheim Logsdon Orkin & Hanson, P.C.

(57) ABSTRACT

A process for producing 2,3,5,6-tetrachloro-1,4-benzenedicarboxylic acid, comprising heating 2,3,5,6-tetrachloro-1,4-benzenedicarboxamide together with sulfuric acid exhibiting an acidity function (—Ho) of 10.27 to 14.44 in the presence of water contained in an amount smaller than a stoichiometric value of hydrolysis at 110 to 190° C. This process efficiently produces 2,3,5,6-tetrachloro-1,4-benzenedicarboxylic acid which is a precursor of dimethyl 2,3,5,6-tetrachloro-1,4-benzenedicarboxylate useful as a herbicide.

4 Claims, No Drawings

PROCESS FOR PRODUCING 2,3,5,6-TETRACHLORO-1,4-BENZENEDICARBOXYLIC ACID

FIELD OF THE INVENTION

The present invention relates to a process for producing 2,3,5,6-tetrachloro-1,4-benzenedicarboxylic acid. More particularly, the present invention relates to a process for producing 2,3,5,6-tetrachloro-1,4-benzenedicarboxylic acid, wherein the formation of reaction by-products is less than in the conventional processes to thereby enable efficiently to produce 2,3,5,6-tetrachloro-1,4-benzenedicarboxylic acid.

BACKGROUND OF THE INVENTION

Dimethyl 2,3,5,6-tetrachloro-1, 4-benzenedicarboxylate is widely and in a large amount used as an agricultural or horticultural herbicide.

A common process for producing dimethyl 2,3,5,6-tetrachloro-1,4-benzenedicarboxylate comprises chlorinating benzene-1,4-dicarbonyl chloride to thereby obtain 2,3,5,6-tetrachloro-1,4-benzenedicarbonyl chloride and converting the same to a dimethyl ester with the use of methanol. However, this process has a drawback in that by-products such as hexachlorobenzene are formed in a large amount.

Therefore, there is a demand for the development of a process for producing dimethyl 2,3,5,6-tetrachloro-1,4-benzenedicarboxylate in which the content of impurities such as the above hexachlorobenzene is greatly reduced.

As the process for producing dimethyl 2,3,5,6-tetrachloro-1,4-benzenedicarboxylate without the formation of hexachlorobenzene, there can be thought out a process comprising first performing an addition of water to 2,3,5,6-tetrachloro-1,4-benzenedicarbonitrile industrially readily procurable to thereby effect synthesis of 2,3,5,6-tetrachloro-1,4-benzenedicarboxamide, subsequently preparing 2,3,5,6-tetrachloro-1,4-benzenedicarboxylic acid from the 2,3,5,6-tetrachloro-1,4-benzenedicarboxamide and thereafter esterifying the 2,3,5,6-tetrachloro-1,4-benzenedicarboxylic acid.

Apart from the above, generally, the method of performing an addition of water to a nitrile in sulfuric acid to thereby obtain a carboxamide and the method of hydrolyzing the carboxamide in sulfuric acid to thereby obtain a carboxylic acid are well known.

However, the hydrolysis of 2,3,5,6-tetrachloro-1,4-benzenedicarboxamide was difficult. Nevertheless, the inventors found that 2,3,5,6-tetrachloro-1,4-benzenedicarboxamide can be hydrolyzed by heating the same in concentrated sulfuric acid at 220° C. or higher temperatures. The hydrolysis of 2,3,5,6-tetrachloro-1,4-benzenedicarboxamide under such severe conditions was unfavorably accompanied by side reactions such as decarboxylation and sulfonation, thereby disenabling to obtain the desired compound, 2,3,5,6-tetrachloro-1,4-benzenedicarboxylic acid, with a high yield.

Therefore, if a method of efficiently producing 2,3,5,6-tetrachloro-1,4-benzenedicarboxylic acid from 2,3,5,6-tetrachloro-1,4-benzenedicarboxamide is developed, its industrial value is extremely great.

An object of the present invention is to provide a process for producing 2,3,5,6-tetrachloro-1, 4-benzenedicarboxylic acid which is a precursor of dimethyl 2,3,5,6-tetrachloro-1,4-benzenedicarboxylate useful as an agricultural or horticultural herbicide. More particularly, an object of the present invention is to provide a process for producing 2,3,5,6-tetrachloro-1,4-benzenedicarboxylic acid from 2,3,5,6-tetrachloro-1,4-benzenedicarbonitrile or 2,3,5,6-tetrachloro-1,4-benzenedicarboxamide as a feedstock, wherein the formation of reaction by-products is less than in the conventional processes to thereby enable the efficient production of 2,3,5,6-tetrachloro-1,4-benzenedicarboxylic acid.

SUMMARY OF THE INVENTION

In one aspect of the present invention, there is provided a process for producing 2,3,5,6-tetrachloro-1,4-benzenedicarboxylic acid, comprising heating 2,3,5,16-tetrachloro-1,4-benzenedicarboxamide at 110 to 190° C. in the presence of sulfuric acid or fuming sulfuric acid containing water in an amount smaller than a stoichiometric value of hydrolysis of 2,3,5,6-tetrachloro-1,4-benzenedicarboxamide.

In another aspect of the present invention, there is provided a process for producing 2,3,5, 6-tetrachloro-1,4-benzenedicarboxylic acid, comprising heating 2,3,5,6-tetrachloro-1,4-benzenedicarbonitrile at 110 to 190° C. in the presence of sulfuric acid or fuming sulfuric acid containing water in an amount smaller than a stoichiometric value required for forming 2,3,5,6-tetrachloro-1,4-benzenedicarboxylic acid from 2,3,5,6-tetrachloro-1,4-benzenedicarbonitrile.

The acidity function (—Ho) of the sulfuric acid or the sulfuric acid containing fuming sulfuric acid is preferably in the range of 10.27 to 14.44.

In the present invention, 2,3,5,6-tetrachloro-1,4-benzenedicarboxylic acid can be obtained directly from industrially readily procurable 2,3,5,6-tetrachloro-1,4-benzenedicarbonitrile or from 2,3,5,6-tetrachloro-1,4-benzenedicarboxamide which can be easily produced therefrom, as a precursor, by heating the same at 110 to 190° C. in the presence of sulfuric acid or fuming sulfuric acid containing water in an amount smaller than a stoichiometric value of hydrolysis. In the present invention, the hydrolysis of 2,3,5,6-tetrachloro-1,4-benzenedicarboxamide is advanced under mild conditions, so that the probability of side reactions is low. Therefore, the present invention enables to produce 2,3,5,6-tetrachloro-1,4-benzenedicarboxylic acid more easily with a higher yield than in the prior art.

DETAILED DESCRIPTION OF THE PREFERRED EMBODIMENTS

The process for producing 2,3,5,6-tetrachloro-1,4-benzenedicarboxylic acid from 2,3,5,6-tetrachloro-1,4-benzenedicarboxamide and the process for producing 2,3,5,6-tetrachloro-1,4-benzenedicarboxylic acid from 2,3,5,6-tetrachloro-1,4-benzenedicarbonitrile according to the present invention will be described separately from each other in detail below.

Production of 2.3,5.6-Tetrachloro-1, 4-benzenedicarboxylic Acid from 2,3,5,6-Tetrachloro-1, 4-benzenedicarboxamide <2,3,5,6-Tetrachloro-1,4-benzenedicarboxamide as a Feedstock>

2,3,5,6-Tetrachloro-1,4-benzenedicarboxamide may be produced from 2,3,5,6-tetrachloro-1,4-benzenedicarbonitrile. 2,3,5,6-Tetrachloro-1,4-benzenedicarbonitrile is being produced on an industrial scale as a feedstock for drugs, agricultural or horticultural herbicides (common name: Tefluthrin, trade name: Force) and industrial chemicals, so that it is available at a low price. The reaction from 2,3,5,6-tetrachloro-1,4-benzenedicarbonitrile to 2,3,5,6-tetrachloro-1,4-benzenedicarboxamide proceeds in acid conditions readily and in a quantitative manner.

<Hydrolysis of 2,3,5,6-Tetrachloro-1,4-benzenedicarboxamide>

The hydrolysis of 2,3,5,6-tetrachloro-1,4-benzenedicarboxamide to obtain 2,3,5,6-tetrachloro-1,4-benzenedicarboxylic acid, effected in the present invention, is carried out in a system consisting of 2,3,5,6-tetrachloro-1,4-benzenedicarboxamide as a feedstock, concentrated sulfuric acid or fuming sulfuric acid and water. Factors influencing the reaction efficiency include the concentration of reactants, temperature, pressure, reaction time, etc. These can be appropriately set individually or in combination.

Concentrated Sulfuric Acid or Fuming Sulfuric Acid

The concentration of concentrated sulfuric acid in use exerts direct influence upon the reaction efficiency by virtue of temperature and time and the yield of desired product. In the hydrolysis of 2,3,5,6-tetrachloro-1,4-benzenedicarboxamide according to the present invention, concentrated sulfuric acid is considered as not only functioning as a catalyst but also supplying water required for the reaction. The first stage of hydrolysis of 2,3,5,6-tetrachloro-1, 4-benzenedicarboxamide is initiated by an addition of proton to the carboxamido group, and a water substitution reaction follows.

Therefore, in the above hydrolysis, a suitable concentration of concentrated sulfuric acid in use is selected taking into account the proton donating capability of concentrated sulfuric acid and the amount of water that is present prior to and during the reaction. In the present invention, use is made of concentrated sulfuric acid containing water in an amount smaller than a stoichiometric value of hydrolysis. For example, concentrated sulfuric acid wherein scarcely any water is contained, or a mixed acid consisting of sulfuric acid and fuming sulfuric acid, is suitable for use as the solvent for conducting the hydrolysis.

The proton donating capability of concentrated sulfuric acid can be expressed by an acidity function, and the acidity function can be measured by the use of Hammett's indicator. For example, the acidity function (—Ho) of 95% sulfuric acid is 9.73. When the hydrolysis of 2,3,5,6-tetrachloro-1,4-benzenedicarboxamide is performed in this sulfuric acid, it is necessary to heat the same at 180° C. or higher temperatures for a prolonged period of time. The acidity function (—Ho) of 100% concentrated sulfuric acid is 11.94, and the acidity function (—Ho) of a mixed acid consisting of sulfuric acid and fuming sulfuric acid is greater than 11.94. In the present invention, it is preferred that the acidity function (—Ho) be in the range of 10.27 to 14.44. When the concentrated sulfuric acid of this acidity function is employed, the hydrolysis efficiently proceeds at 110 to 190° C. It is still preferred that the acidity function (—Ho) be in the range of 10.57 to 13.00.

Although the amount of concentrated sulfuric acid or fuming sulfuric acid is not particularly limited, it is preferred from the viewpoint of the requirement for desirably maintaining the agitation of solution all of the time during the reaction and from the viewpoint of productivity per batch that 2 to 10 parts by weight, especially 2.5 to 6 parts by weight, of concentrated sulfuric acid or fuming sulfuric acid be used per part by weight of 2,3,5,6-tetrachloro-1,4-benzenedicarboxamide.

Water that Participates in the Reaction

Theoretically, 2 mol of water is needed in the hydrolysis of 2,3,5,6-tetrachloro-1, 4-benzenedicarboxamide. However, as described later, the presence of 2 mol or more of water prior to the reaction causes the hydrolysis to become extremely difficult. For advancing the reaction under the conditions, it is necessary to heat 2,3,5,6-tetrachloro-1,4-benzenedicarboxamide at high temperatures, for example, 220° C. or higher. By contrast, in the present invention, the hydrolysis of 2,3,5,6-tetrachloro-1, 4-benzenedicarboxamide is performed in the presence of water whose amount is smaller than the stoichiometric value of hydrolysis of 2,3,5,6-tetrachloro-1,4-benzenedicarboxamide. This enables the performance of the above reaction at 110 to 190° C. For example, the amount of water which is present prior to the reaction is not limited as long as it is smaller than the stoichiometric value of hydrolysis, i.e., 2 mol. Further reduction of the amount of water is preferred. It is especially preferred that the amount of water be as minute as near to 0 mol. With respect to the water remaining in sulfuric acid, when, for example, fuming sulfuric acid is added, the reaction proceeds leftwards in the following formula so as to form $H_2SO_4$ with the result that the amount of water becomes as minute as near to 0 mol:

(IV)

Apart from the above, even purified sulfuric acid, in the equilibrium, contains a multiplicity of chemical species, and it is considered that water molecules, although the amount thereof is close to a trace, do exist in the sulfuric acid. Thus, it is presumed that the water produced by the decomposition of sulfuric acid resulting from the rightward advance in the above equilibrium formula (IV) will be supplied to the reaction system in order to compensate for the water consumed by the hydrolysis.

The advance of hydrolysis of 2,3,5, 6-tetrachloro-1,4-benzenedicarboxamide in concentrated sulfuric acid or fuming sulfuric acid according to the present invention is not known at all.

The reaction condition preferably employed for accelerating the hydrolysis at 190° C. or below at the initiation or during the reaction is to cause water to be present in an extremely minute amount. Accordingly, it is desirable to use 2 to 10 parts by weight of concentrated sulfuric acid or fuming sulfuric acid per part by weight of 2,3,5,6-tetrachloro-1, 4-benzenedicarboxamide, as aforementioned.

Temperature

The temperature required for the hydrolysis of 2,3,5,6-tetrachloro-1,4-benzenedicarboxamide is conspicuously varied depending on the amount of water contained in sulfuric acid as aforementioned. Thus, in the hydrolysis of this compound in the sulfuric acid specified in the present invention, it is preferred that the temperature be in the range of 110 to 190° C., especially 120 to 185° C., and still especially 130 to 180° C. When the temperature falls within these ranges, not only does the hydrolysis of 2,3,5,6-tetrachloro-1,4-benzenedicarboxamide rapidly proceed but also the yield of 2,3,5,6-tetrachloro-1,4-benzenedicarboxylic acid is high.

Contrarily when a large amount of water is present prior to or during the reaction, the hydrolysis would not proceed with practical speed at 190° C. or below. For ensuring the advance of reaction in this condition, it is requisite to heat the reactant at severe temperatures such as 220° C. or higher. At these high temperatures, it cannot necessarily be assured that the desired compound is produced without the occurrence of undesirable side reactions such as decarboxylation or sulfonation of formed 2,3,5,6-tetrachloro-1, 4-benzenedicarboxylic acid.

Specifically, when the 2,3,5,6-tetrachloro-1,4-benzenedicarboxamide is hydrolyzed at 220° C. in sulfuric acid, the formation of by-products attributed to the decarboxylation reaction results in unsatisfactory purity for a technical product for agricultural chemicals or their intermediates. A further serious problem is that heating at 220° C. or higher temperatures while using sulfuric acid can be accomplished only by the employment of very special and very expensive facilities to thereby make it difficult to produce the desired compound at low cost.

Therefore, in the hydrolysis of 2,3,5,6-tetrachloro-1,4-benzenedicarboxamide, performing the reaction in concentrated sulfuric acid or fuming sulfuric acid containing water in an amount smaller than a stoichiometric value of hydrolysis is preferred from the viewpoint that the hydrolysis can be effected at relatively low temperature on a practical production level.

Reaction Time

The reaction time is influenced by the temperature and the amount of water contained, as aforementioned. Regulating the amount of water contained to a minute level in the initial stage of the reaction and further controlling the reaction temperature at 110 to 190° C. is favorable from the viewpoint of industrial production because the reaction time falls within the range of 5 min to 24 hr. Lowering the reaction temperature to below 110° C. results in a prolonged reaction time, thereby causing a practicability deterioration.

Progress of Reaction

In the hydrolysis of 2,3,5,6-tetrachloro-1, 4-benzenedicarboxamide in sulfuric acid, 2,3,5, 6-tetrachloro-1,4-benzenedicarboxylic acid is formed and, after the reaction, precipitated out of the reaction system. Further, when the hydrolysis is advanced, for compensating for consumed water, the above equilibrium of formula (IV) is inclined rightwards to thereby produce water. The water produced by the decomposition of sulfuric acid is consumed as a further reactant. Simultaneously; $SO_3$ which would not have direct participation in the reaction is formed in an amount corresponding to the amount of consumed water. In the present invention, the reaction is performed in an open system and is advanced under atmospheric pressure. $SO_3$ formed in the course of the reaction as seen from the formula (IV) is liberated in accordance with the progress of the hydrolysis. Because of the open system, the $SO_3$ is released from the system. This further facilitates the progress of the hydrolysis.

Production of 2,3,5,6-Tetrachloro-1, 4-benzenedicarboxylic Acid from 2,3,5,6-Tetrachloro-1, 4-benzenedicarbonitrile In the present invention, in the production of 2,3,5,6-tetrachloro-1,4-benzenedicarboxylic acid from 2,3,5,6-tetrachloro-1,4-benzenedicarbonitrile as well, it is preferred that 2,3,5,6-tetrachloro-1, 4-benzenedicarbonitrile be heated at 110 to 190° C. in the presence of sulfuric acid or fuming sulfuric acid containing water in an amount smaller than a stoichiometric value required for forming 2,3,5, 6-tetrachloro-1,4-benzenedicarboxylic acid from 2,3,5, 6-tetrachloro-1,4-benzenedicarbonitrile.

Specifically, in the reaction from 2,3,5,6-tetrachloro-1,4-benzenedicarbonitrile to 2,3,5,6-tetrachloro-1,4-benzenedicarboxamide, 2 mol of water is consumed per mol of the above carbonitrile compound. In the hydrolysis of 2,3,5,6-tetrachloro-1,4-benzenedicarboxamide to thereby obtain 2,3,5,6-tetrachloro-1,4-benzenedicarboxylic acid, 2 mol of water is consumed per mol of the above carboxamide compound. Therefore, theoretically, the total amount of water required for forming 2,3,5,6-tetrachloro-1, 4-benzenedicarboxylic acid from 2,3,5,6-tetrachloro-1, 4-benzenedicarbonitrile is 4 mol.

However, in the present invention, the amount of water required for carrying out the reactions from 2,3,5,6-tetrachloro-1,4-benzenedicarbonitrile to 2,3,5,6-tetrachloro-1,4-benzenedicarboxylic acid is satisfactory, with a proviso that it is smaller than the stoichiometric value required for forming 2,3,5,6-tetrachloro-1,4-benzenedicarboxylic acid from 2,3,5,6-tetrachloro-1,4-benzenedicarbonitrile, i.e., 4 mol.

In the present invention, 2,3,5,6-tetrachloro-1, 4-benzenedicarboxylic acid that is useful as a herbicide precursor can be produced with a high yield by a simple operation comprising hydrolyzing readily procurable cheap 2,3,5,6-tetrachloro-1,4-benzenedicarbonitrile as a feedstock in sulfuric acid (preferably, sulfuric acid containing fuming sulfuric acid) in the presence of water whose amount is smaller than the stoichiometric value of the hydrolysis. Furthermore, in the process of the present invention, from the 2,3,5,6-tetrachloro-1,4-benzenedicarboxamide which, in the presence of water whose amount is not smaller than the stoichiometric value of the hydrolysis, would not be hydrolyzed unless heated at 220° C. or higher temperatures in sulfuric acid, 2,3,5,6-tetrachloro-1, 4-benzenedicarboxylic acid can be efficiently produced without the occurrence of side reactions under mild reaction conditions including lower temperatures of 110 to 190° C.

EXAMPLE

The present invention will further be illustrated below with reference to the following Examples and Comparative Examples, which are, however, only for illustrative embodying purposes and in no way limit the scope of the invention since the scope of the invention is to be determined by the appended claims.

Example 1

Preparation of 2,3,5,6-Tetrachloro-1, 4-benzenedicarboxylic Acid (Compound 2) from 2,3, 5, 6-Tetrachloro-1,4-benzenedicarboxamide (Compound 1)

6.04 g (0.02 mol) of 2,3,5,6-tetrachloro-1, 4-benzenedicarboxamide and 17.65 g of sulfuric acid, consisting of 12.43 g of 96.3% sulfuric acid (containing 0.0256 mol of water) and 5.22 g of 26% fuming sulfuric acid (containing 0.017 mol of $SO_3$), were charged into a reactor, and a hydrolysis of 2,3,5,6-tetrachloro-1,4-benzenedicarboxamide was performed at 180° C. for 6 hr under atmospheric pressure. The amount of water which was present prior to the reaction was 0.0086 mol because the $SO_3$ in fuming sulfuric acid and the water in sulfuric acid were converted to sulfuric acid according to the formula (IV). After the completion of the reaction, precipitated crystals were collected by filtration, washed with water, and dried. As a result, 2,3,5,6-tetrachloro-1,4-benzenedicarboxylic acid was obtained.

Yield: 5.8 g (isolation yield 95%), and IR (KBr): 770, 795, 875, 1240, 1330, 1355, 1435, 1640, 1705, and 2470 cm$^{-1}$.

The infrared spectroscopy was conducted with the use of potassium bromide.

Example 2

Preparation of 2,3,5,6-Tetrachloro-1, 4-benzenedicarboxylic Acid (Compound 2) from 2,3, 5, 6-Tetrachloro-1,4-benzenedicarboxamide (Compound 1)

6.04 g (0.02 mol) of 2,3,5,6-tetrachloro-1,4-benzenedicarboxamide and 17.64 g of sulfuric acid, consisting of 10.82 g of 96.3% sulfuric acid and 6.82 g of 26% fuming sulfuric acid, were charged into a reactor, and a hydrolysis of 2,3,5,6-tetrachloro-1,4-benzenedicarboxamide was performed under atmospheric pressure. The temperature and reaction time were as specified in Table 1. After the completion of the reaction, the same processing as in Example 1 was conducted. As a result, 2,3,5,6-tetrachloro-1,4-benzenedicarboxylic acid was obtained.

Yield: 5.9 g (isolation yield 97%), and IR (KBr): same as in Example 1.

Example 3

Preparation of 2,3,5,6-Tetrachloro-1, 4-benzenedicarboxylic Acid (Compound 2) from 2,3, 5, 6-tetrachloro-1,4-benzenedicarboxamide (Compound 1)

6.04 g (0.02 mol) of 2,3,5,6-tetrachloro-1,4-benzenedicarboxamide and 17.65 g of sulfuric acid, consisting of 4.64 g of 96.3% sulfuric acid and 13.01 g of 26% fuming sulfuric acid, were charged into a reactor, and a hydrolysis of 2,3,5,6-tetrachloro-1,4-benzenedicarboxamide was performed under atmospheric pressure. The temperature and reaction time were as specified in Table 1. After the completion of the reaction, the same processing as in Example 1 was conducted. As a result, 2,3,5, 6-tetrachloro-1,4-benzenedicarboxylic acid was obtained.

Yield: 4.1 g (isolation yield 68%), and IR (KBr): same as in Example 1.

Example 4

Preparation of 2,3,5,6-Tetrachloro-1, 4-benzenedicarboxylic Acid (Compound 2) from 2,3, 5, 6-tetrachloro-1,4-benzenedicarboxamide (compound 1)

6.04 g (0.02 mol) of 2,3,5,6-tetrachloro-1,4-benzenedicarboxamide and 17.65 g of 98.0% sulfuric acid were charged into a reactor, and a hydrolysis of 2,3,5 6-tetrachloro-1,4-benzenedicarboxamide was performed under atmospheric pressure. The temperature and reaction time were as specified in Table 1. After the completion of the reaction, the same processing as in Example 1 was conducted. As a result, 2,3,5, 6-tetrachloro-1,4-benzenedicarboxylic acid was obtained.

Yield: 5.8 g (isolation yield 95%), and IR (KBr): same as in Example 1.

Example 5

Preparation of 2,3,5,6-Tetrachloro-1,1, 4-benzenedicarboxylic Acid (Compound 2) from 2,3, 5, 6-Tetrachloro-1,4-benzenedicarboxamide (Compound 1)

6.04 g (0.02 mol) of 2,3,5,6-tetrachloro-1,4-benzenedicarboxamide and 17.65 g of 99.99% sulfuric acid were charged into a reactor, and a hydrolysis of 2,3,5,6-tetrachloro-1,4-benzenedicarboxamide was performed under atmospheric pressure. The temperature and reaction time were as specified in Table 1. After the completion of the reaction, the same processing as in Example 1 was conducted. As a result, 2,3,5,6-tetrachloro-1,4-benzenedicarboxylic acid was obtained.

Yield: 5.5 g (isolation yield 90%), and IR (KBr): same as in Example 1.

Comparative Example 1

Preparation of 2,3,5,6-tetrachloro-1, 4-benzenedicarboxylic Acid (Compound 2) from 2,3, 5, 6-Tetrachloro-1,4-benzenedicarboxamide (Compound 1)

6.04 g (0.02 mol) of 2,3,5,6-tetrachloro-1,4-benzenedicarboxamide and 17.65 g of 95.0% sulfuric acid were charged into a reactor, and a hydrolysis of 2,3,5,6-tetrachloro-1,4-benzenedicarboxamide was performed under atmospheric pressure. The temperature and reaction time were as specified in Table 1. However, any desired crystals of 2,3,5,6-tetrachloro-1, 4-benzenedicarboxylic acid were not precipitated.

Yield: 0 g (isolation yield 0%).

Example 6

Preparation of 2,3,5,6-Tetrachloro-1, 4-benzenedicarboxylic Acid (Compound 2) from 2,3, 5, 6-Tetrachloro-1,4-benzenedicarbonitrile (Compound 3)

5.32 g (0.02 mol) of 2,3,5,6-tetrachloro-1,4-benzenedicarbonitrile and 17.65 g of sulfuric acid, consisting of 11.06 g of 90.0% sulfuric acid and 6.59 g of 26% fuming sulfuric acid, were charged into a reactor, and a hydrolysis of 2,3,5,6-tetrachloro-1, 4-benzenedicarbonitrile was performed at 160° C. for 3 hr under atmospheric pressure. After the completion of the reaction, precipitated crystals were collected by filtration, washed with water, and dried. As a result, 2,3,5,6-tetrachloro-1,4-benzenedicarboxylic acid was obtained.

Yield: 5.9 g (isolation yield 97%), and IR (KBr): same as in Example 1.

Comparative Example 2

Preparation of 2,3,5,6-Tetrachloro-1, 4-benzenedicarboxylic Acid (Compound 2) from 2,3, 5, 6-tetrachloro-1,4-benzenedicarbonitrile (Compound 3)

5.32 g (0.02 mol) of 2,3,5,6-tetrachloro-1,4-benzenedicarbonitrile and 17.65 g of 90.0% sulfuric acid were charged into a reactor, and a hydrolysis of 2,3,5,6- tetrachloro-1,4-benzenedicarbonitrile was performed under atmospheric pressure. The temperature and reaction time were as specified in Table 1. However, any desired crystals of 2,3,5,6-tetrachloro-1, 4-benzenedicarboxylic acid were not precipitated.

Yield: 0 g (isolation yield 0%).

Comparative Example 3

Preparation of 2,3,5,6-Tetrachloro-1, 4-benzenedicarboxylic Acid (Compound 2) from 2,3, 5, 6-Tetrachloro-1,4-benzenedicarbonitrile (Compound 3)

5.32 g (0.02 mol) of 2,3,5,6-tetrachloro-1, 4-benzenedicarbonitrile and 17.65 g of 90.0% sulfuric acid were charged into a reactor, and a hydrolysis of 2,3,5,6-tetrachloro-1,4-benzenedicarbonitrile was performed under atmospheric pressure. The temperature and reaction time were as specified in Table 1. After the completion of the reaction, the same processing as in Example 1 was conducted. As a result, 2,3,5, 6-tetrachloro-1,4-benzenedicarboxylic acid was obtained.

Yield: 5.9 g (isolation yield 97%), and IR (KBr): same as in Example 1.

Table 1 lists results of the syntheses of Examples 1 to 6 and Comparative Examples 1 to 3 wherein 2,3, 5,6-tetrachloro-1,4-benzenedicarboxylic acid (compound 2) was prepared by reacting 0.02 mol of the starting material, i.e., 2,3,5,6-tetrachloro-1, 4-benzenedicarboxamide (compound 1) or 2,3,5, 6-tetrachloro-1,4-benzenedicarbonitrile (compound 3) in a given amount of sulfuric acid at a given temperature for a given period of time.

6-tetrachloro-1,4-benzenedicarboxamide at 180 or 130° C. for 7 or 27 hr.

In Examples 1 to 3, the hydrolysis of 2,3,5, 6-tetrachloro-1,4-benzenedicarboxamide occurred in sulfuric acid containing fuming sulfuric acid even in the absence of 2 mol, stoichiometric amount, of water added from outside per mol of 2,3,5,6-tetrachloro-1, 4-benzenedicarboxamide, and the reaction proceeded at 180° C. or lower temperatures, thereby forming desired 2,3,5,6-tetrachloro-1,4-benzenedicarboxylic acid.

However, as is apparent from Comparative Example 1, 2,3,5,6-tetrachloro-1,4-benzenedicarboxylic acid was not formed at all by heating 2,3,5,6-tetrachloro-1, 4-benzenedicarboxamide in 95% sulfuric acid (acidity function 9.73) at 180° C. for 24 hr.

Therefore, in the hydrolysis of 2,3,5, 6-tetrachloro-1,4-benzenedicarboxamide according to the present invention, the reaction proceeds in sulfuric acid or fuming sulfuric acid containing water in an amount smaller than the stoichiometric value of hydrolysis, and, under this condition, the requisite temperature can be lowered remarkably. Preferred temperature is in the range of 110 to 190° C., and using sulfuric acid containing an extremely minute amount of water is especially preferred.

For obtaining 2,3,5,6-tetrachloro-1, 4-benzenedicarboxylic acid from 2,3,5,6-tetrachloro-1, 4-benzenedicarbonitrile, theoretically, 4 mol of water is required per mol of 2,3,5,6-tetrachloro-1, 4-benzenedicarbonitrile. However, in the present invention, desired 2,3,5,6-tetrachloro-1, 4-benzenedicarboxylic acid was efficiently obtained in one step by heating 2,3,5,6-tetrachloro-1, 4-benzenedicarbonitrile at 160° C. for 3 hr in

TABLE 1

| | Compd. (1) mol | Water contd. in conc. sulfuric acid or fuming sulfuric acid mol | Sulfuric acid or sulfuric acid contg. fuming sulfuric acid (acidity function) | Temp. °C. | Time h | Compd. (2) mol | Yield % |
|---|---|---|---|---|---|---|---|
| Example 1 | 0.02 | 0.0086 | fuming sulfuric acid (11.32) | 180 | 6 | 0.0190 | 95 |
| Example 2 | 0.02 | 0.0001 | fuming sulfuric acid (11.44) | 160 | 3 | 0.0194 | 97 |
| Example 3 | 0.02 | about 0 | fuming sulfuric acid (12.8) | 155 | 3 | 0.0135 | 68 |
| Example 4 | 0.02 | 0.0196 | sulfuric acid (10.27) | 180 | 7 | 0.019 | 95 |
| Example 5 | 0.02 | about 0 | sulfuric acid (11.44) | 130 | 27 | 0.015 | 90 |
| Comp.Ex.1 | 0.02 | 0.0490 | sulfuric acid (9.73) | 180 | 24 | — | 0 |
| | Compd. (3) mol | | | | | | |
| Example 6 | 0.02 | 0.040 | fuming sulfuric acid (11.44) | 160 | 3 | 0.0194 | 97 |
| Comp. Ex. 2 | 0.02 | 0.098 | sulfuric acid (10.20) | 180 | 12 | 0.0 | 0 |
| Comp. Ex. 3 | 0.02 | 0.098 | sulfuric acid (10.20) | 220 | 8 | 0.0194 | 97 |

In the hydrolysis of 2,3,5,6-tetrachloro-1, 4-benzenedicarboxamide, as is apparent from Examples 4 and 5, the maximum reduction of the amount of water in sulfuric acid resulted in efficiently forming desired 2,3,5,6-tetrachloro-1,4-benzenedicarboxylic acid by heating 2,3,5, the presence of sulfuric acid and fuming sulfuric acid containing water in an amount smaller than the stoichiometric value of hydrolysis, as apparent from Example 6.

In contrast, as is apparent from Comparative Example 3, desired 2,3,5,6-tetrachloro-1,4-benzenedicarboxylic acid was formed with a high yield substantially without the occurrence of any side reactions even by heating 2,3,5,6-tetrachloro-14-benzenedicarbonitrile at such a high temperature as 220° C. at which ordinary organic compounds would be decomposed. However, under this condition, the reaction temperature is too high to be suitable for industrial production.

Therefore, for obtaining 2,3,5,6-tetrachloro-1,4-benzenedicarboxylic acid in one step from 2,3,5,6-tetrachloro-1,4-benzenedicarbonitrile as a starting material, it is preferred to use sulfuric acid whose acidity function (—Ho) is in the range of 10.27 to 14.44 in the presence of water contained in an amount smaller than the stoichiometric value of hydrolysis per mol of 2,3,5,6-tetrachloro-1,4-benzenedicarbonitrile.

What is claimed is:

1. A process for producing 2,3,5,6-tetrachloro-1,4-benzenedicarboxylic acid of the formula:

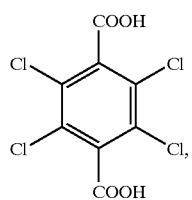
(II)

which process comprises heating 2,3,5,6-tetrachloro-1,4-benzenedicarboxamide at 110 to 190° C. in the presence of sulfuric acid or fuming sulfuric acid exhibiting an acidity function (—H$_o$) of 10.27 to 14.44 and containing water in an amount substantially smaller than a stoichiometric value of hydrolysis of 2,3,5,6-tetrachloro-1, 4-benzenedicarboxamide, said 2,3,5,6-tetrachloro-1,4-benzenedicarboxamide represented by the formula:

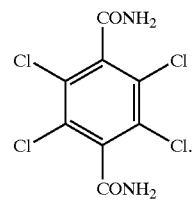
(I)

2. The process as claimed in claim 1, wherein the said sulfuric acid or fuming sulfuric acid exhibits an acidity function (—Ho) of 10.27 to 14.44.

3. A process for producing 2,3,5,6-tetrachloro-1,4-benzenedicarboxylic acid, comprising heating 2,3,5,6-tetrachloro-1,4-benzenedicarbonitrile at 110 to 190° C. in the presence of sulfuric acid or fuming sulfuric acid exhibiting an acidity function (—H$_0$ of 10.27 to 14.44 and containing water in an amount substantially smaller than a stoichiometric value required for forming 2,3,5,6-tetrachloro-1,4-benzenedicarboxylic acid from 2,3,5,6-tetrachloro-1,4-benzenedicarbonitrile, said 2,3,5,6-tetrachloro-1, 4-benzenedicarbonitrile represented by the formula:

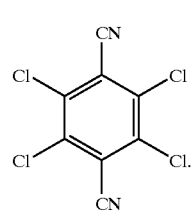
(III)

4. The process as claimed in claim 3, wherein the said sulfuric acid or fuming sulfuric acid exhibits an acidity function (—Ho) of 10.27 to 14.44.

* * * * *

UNITED STATES PATENT AND TRADEMARK OFFICE
CERTIFICATE OF CORRECTION

PATENT NO. : 6,452,046 B2 Page 1 of 1
DATED : September 17, 2002
INVENTOR(S) : Utaro Matsushita et al.

It is certified that error appears in the above-identified patent and that said Letters Patent is hereby corrected as shown below:

Column 2,
Lines 13-14, "2,3,5,16-tetrachloro-1,4-benzenedicarboxamide" should read
-- 2,3,5,6-tetrachloro-1,4-benzenedicarboxamide --.

Column 5,
Line 50, "Simultaneously;" should read -- Simultaneously, --.

Column 7,
Line 7, "cm$^1$" should read -- cm$^{-1}$ --.

Column 8,
Lines 6-7, "2,3,5,6-Tetrachloro-1,1,4-benzenedicarboxylic" should read
-- 2,3,5,6-tetrachloro-1,4-benzenedicarboxylic --.

Column 11,
Lines 2-3, "2,3,5,6-tetrachloro-14-benzenedicarbonitrile" should read
-- 2,3,5,6-tetrachloro-1,4-benzenedicarbonitrile --.

Signed and Sealed this

Twenty-fifth Day of February, 2003

JAMES E. ROGAN
*Director of the United States Patent and Trademark Office*